(12) United States Patent
Loncar et al.

(10) Patent No.: US 9,199,056 B2
(45) Date of Patent: Dec. 1, 2015

(54) DEVICE, AN AGGREGATE AND A METHOD FOR PROVIDING A GASIFIED ANESTHETIC AGENT

(75) Inventors: Mario Loncar, Ekerö (SE); Mats Wallin, Spånga (SE); Christer Ahlmén, Sollentuna (SE)

(73) Assignee: Maquet Critical Care AB, Solna (SE)

( * ) Notice: Subject to any disclaimer, the term of this patent is extended or adjusted under 35 U.S.C. 154(b) by 1117 days.

(21) Appl. No.: 13/144,467

(22) PCT Filed: Jan. 19, 2010

(86) PCT No.: PCT/EP2010/050598
§ 371 (c)(1),
(2), (4) Date: Sep. 28, 2011

(87) PCT Pub. No.: WO2010/081914
PCT Pub. Date: Jul. 22, 2010

(65) Prior Publication Data
US 2012/0031402 A1    Feb. 9, 2012

(30) Foreign Application Priority Data
Jan. 19, 2009    (SE) ..................... 0950013

(51) Int. Cl.
*A61M 16/18*    (2006.01)
*A61M 16/01*    (2006.01)
A61M 16/00    (2006.01)
A61M 16/10    (2006.01)

(52) U.S. Cl.
CPC .............. *A61M 16/18* (2013.01); *A61M 16/01* (2013.01); *A61M 16/009* (2013.01); *A61M 16/0078* (2013.01); *A61M 16/1045* (2013.01); *A61M 2202/048* (2013.01)

(58) Field of Classification Search
CPC ... A61M 16/01; A61M 16/104; A61M 16/18; A61M 2016/103; A61M 2016/1035
USPC ............. 128/200.14, 203.12–203.14, 204.18, 128/204.21, 204.23
See application file for complete search history.

(56) References Cited

U.S. PATENT DOCUMENTS

| 4,279,250 | A | * | 7/1981 | Valenta et al. | ........... | 128/200.14 |
| 5,727,545 | A | * | 3/1998 | Psaros | ...................... | 128/203.12 |
| 5,782,233 | A | * | 7/1998 | Niemi et al. | ............. | 128/202.22 |

(Continued)

FOREIGN PATENT DOCUMENTS

| EP | 0 745 404 | 12/1996 |
| WO | WO 94/08650 | 4/1994 |
| WO | WO 2004/028607 | 4/2004 |

*Primary Examiner* — Valerie L Skorupa
(74) *Attorney, Agent, or Firm* — Schiff Hardin LLP

(57) ABSTRACT

A respiratory anesthetic aggregate devised for coupling to a breathing apparatus has an anesthetic gasifier unit that has a breathing gas input port connected to a first point in an inspiratory patient gas delivery path of a breathing apparatus, and a fresh gas output port connected to a second point in the patient gas delivery path downstream the first point. The inspiratory patient gas delivery path is connected via a mainstream connection between the first and second point. Thereby the anesthetic gasifier unit is connected in a sidestream configuration to the patient gas delivery path for adding the gasified anesthetic agent in a desired concentration to the patient gas delivery path at the second point. When aggregate is coupled to a breathing apparatus, a substantially volume neutral delivery of anesthetic agent is provided to the breathing apparatus.

24 Claims, 6 Drawing Sheets

(56) References Cited

U.S. PATENT DOCUMENTS

| | | |
|---|---|---|
| 6,155,255 A | 12/2000 | Lambert |
| 6,230,666 B1 | 5/2001 | Wallin et al. |
| 6,874,502 B1 * | 4/2005 | Nashed .................. 128/205.23 |
| 7,077,136 B2 * | 7/2006 | Ahlmen et al. .......... 128/205.27 |
| 2004/0154617 A1 * | 8/2004 | Enk .......................... 128/203.12 |
| 2006/0062737 A1 | 3/2006 | Hofmann et al. |
| 2009/0095291 A1 * | 4/2009 | Wruck ..................... 128/203.12 |
| 2009/0250054 A1 * | 10/2009 | Loncar et al. ............ 128/203.14 |
| 2009/0293872 A1 | 12/2009 | Bocke |
| 2011/0000488 A1 * | 1/2011 | Blomberg ................ 128/203.14 |

* cited by examiner

DEVICE, AN AGGREGATE AND A METHOD FOR PROVIDING A GASIFIED ANESTHETIC AGENT

BACKGROUND OF THE INVENTION

1. Field of the Invention

This invention pertains in general to the field of breathing apparatuses. More particularly the invention relates to a device, aggregate and/or method for providing a gasified anesthetic agent by means of a breathing apparatus.

2. Description of the Prior Art

Certain anesthetic vaporizers for liquid anesthetic agents are known from the prior art.

For instance, in U.S. Pat. No. 6,230,666 an anesthetic vaporizer is disclosed for an anesthesia machine.

However, anesthetic vaporizers are hitherto provided as integrated units in rather costly anesthesia workstations. In addition, there have been previous systems based on intensive care ventilators with added anesthesia capability, such as the Siemens-Elema Servo Ventilator 900C. However, these systems were not providing a volume neutral delivery of gasified anesthetic agents, due to an additional fresh gas flow provided in addition to an inspiratory flow of gas from the ventilator. The anesthetic agent supplied to the patient needs a carrier gas, usually a mixture of $O_2$ and/or air and/or nitrous oxide, into which the anesthetic agent is gasified, usually from a liquid state. The gasified anesthetic agent is then added, together with a volume of the carrier gas, to a flow of breathing gas in a breathing circuit, to which the patient is connected. This volume is often larger than the volume of carbon dioxide removed from the breathing circuit in the carbon dioxide absorber, and the surplus will be sent into to the evac system, usually via a so called pop off valve relieving pressure over a certain threshold in the breathing circuit. The flow of carrier gas is the aforementioned fresh gas flow, and is provided to pass an anesthetic gasifier unit. Therefore, the gasified anesthetic agents are not provided in a way of volume neutral delivery with reference to the flow of breathing gas. However, non-volume neutral delivery of anesthetic agent often results in a loss of anesthetic agent to the evac system due to the extra volume.

Thus, there is a need for a new anesthetic gasifier unit or aggregate having modular capabilities for use with breathing apparatuses, such as intensive care ventilators, and providing a substantially volume neutral supply of anesthetic agent to a breathing gas delivered to a patient.

Anesthetic vaporizers for direct injection of a liquid anesthetic agent into a mainstream of gas delivered to a patient are for instance disclosed in U.S. Pat. No. 6,155,255 of Hans Lambert. However such mainstream arrangements have some major disadvantages. One issue is that liquid agent that is not fully vaporized may be present in the mainstream to the patient. Droplets or aerosol of liquid anesthetic agent leads to several complications. One complication is that gas analyzers may render less reliable measurement results for non gaseous components. Thus, a feedback control of the agent concentration may be erroneous and the patient safety may be risked by too high administered anesthetic drug concentrations, i.e. the mainstream vaporizer of U.S. Pat. No. 6,155,255 may provide non-desired high doses. Another issue is handling safety of the device of U.S. Pat. No. 6,155,255. Clinical care personal may disconnect the tubing in which the device of U.S. Pat. No. 6,155,255 is arranged while it still is injecting liquid anesthetic agent. The anesthetic agent will thus be delivered uncontrolled to the surrounding environment by continued injection of liquid anesthetic agent. In this case, persons in the ambient environment, risk being subjected to the anesthetic agent, which might have dire health consequences.

Thus, there is also a need of providing an anesthetic delivery device for gaseous anesthetic agents having improved safety. Safety includes patient safety and/or safety of clinical personal, as well as reliability of the apparatus.

Hence, an improved anesthetic gasifier unit or modular aggregate comprising such an anesthetic gasifier unit would be advantageous and in particular allowing for increased flexibility, cost-effectiveness, patient safety, user friendliness and safety, and/or efficiency would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing aspects of the invention embodied in an anesthetic gasifier unit, a respiratory anesthetic aggregate, a breathing apparatus, a method, and a computer program product, according to the appended patent claims.

An anesthetic agent is provided in a breathing circuit by volume neutral addition into the breathing circuit. This addition of gaseous anesthetic agent is provided in a controlled manner. The volume neutral addition is provided by a sidestream arrangement of an anesthetic gasifier unit in relation to a mainstream flow of breathing gas in a breathing circuit.

Anesthetic agents comprise anesthetic agents suitable for gasification. Such anesthetic agents are for instance the commonly used halogenated fluorocarbon based anesthetic agents, such as commercially available as Halothane, Isofluarane™, Enflurane™, Sevoflurane™, or Desflurane™. These agents are usually provided as liquids for gasification in inhalational anesthesia. A mixture of these may be provided in certain cases, for instance by providing a plurality of anesthetic gasifier units.

Some embodiments of the invention provide for a substantially volume neutral delivery of anesthetic agent for inhalational anesthesia.

This volume neutrality is provided by an anesthetic gasifier unit adapted to supply gasified anesthetic agent with a carrier gas supply from a first point connected via a mainstream connection with a second point of a breathing circuit. The carrier gas is provided to the anesthetic gasifier unit in a sidestream flow of carrier gas. Hereinafter, the carrier gas with added gasified anesthetic agent is referenced to as "fresh gas", using this wording, traditionally used in connection with circle breathing circuits, in the context of the present application. The anesthetic gasifier unit is further adapted to provide the gasified anesthetic agent to the second point in a volume neutral manner. In more detail, the total gas flow passing the first point into both the mainstream connection and the sidestream connection to the anesthetic gasifier unit is substantially equal to the recombined gas flow, enriched with the gasified anesthetic agent, at the second point. The volume of the gasified anesthetic agent in relation to the volume of the fresh gas, or the total volume of breathing gas delivered to the patient, is very low or negligible. Hence, no unnecessary or undesired volume of gas is added.

According to a first aspect of the invention, a respiratory anesthetic aggregate is provided that is devised for coupling to a breathing apparatus. The aggregate includes an anesthetic gasifier unit adapted to gasify an anesthetic agent, and has a breathing gas input port and a fresh gas output port. The breathing gas input port is in operation connected to a first point in an inspiratory patient gas delivery path of the breathing apparatus by means of a breathing gas input line. The fresh gas output port is in operation connected to a second point in the inspiratory patient gas delivery path via a fresh gas output line thereof. The second point is arranged downstream the first point in the inspiratory patient gas delivery path, wherein the inspiratory patient gas delivery path is connected via a mainstream connection of breathing gas between the first and second point. Thus the anesthetic gasifier unit in use is connected in a sidestream configuration to the inspiratory patient gas delivery path for adding the gasified anesthetic agent in a desired concentration to the inspiratory patient gas delivery path at the second point. The aggregate further includes a flow generator unit for providing a flow of breathing gas from the first point to the breathing gas input port of the anesthetic gasifier unit.

The aggregate is adapted to provide the gasified anesthetic agent at the second point as a fresh gas output in a volume neutral manner.

In embodiments, the aggregate has the gas input line connected to the inspiratory patient gas delivery path upstream a Y-piece to an inspiratory line. In this manner the anesthetic gasifier unit is in operation advantageously provided with $CO_2$ free and by the patient uncontaminated gas at the breathing gas input port.

In some embodiments the second point is arranged and connected to a common inspiration and expiration patient connection line of the inspiratory patient gas delivery path downstream the Y-piece. In some embodiments the second point is arranged and connected to the inspiratory line.

In embodiments the first point is arranged at a distance from the second point. The inspiratory patient gas delivery path is comprised in a breathing circuit connected to the breathing apparatus. In some embodiments a reflector known in the art is arranged between the first point and the second point, and the first point is arranged and connected to the inspiratory patient gas delivery path upstream a Y-piece to the inspiratory line and the second point is arranged and connected to a patient connection line downstream the Y-piece.

In some embodiments a mainstream volume is arranged between the first point and the second point and both the first point and the second point are arranged and connected to the inspiratory line of the inspiratory patient gas delivery path upstream the Y-piece. The latter embodiments are particularly advantageous with regard to no added dead space and are operated with neonatal or pediatric patients having small minute volumes In some embodiments the flow generator unit is adapted to provide a rate of the flow of breathing gas to the anesthetic gasifier unit from the first point that is less than a flow of gas supplied through the inspiratory patient gas delivery path by the breathing apparatus to the first point. In this manner a flow of gas via the mainstream connection towards the patient is larger than zero when the flow generator unit in operation provides a flow of breathing gas from the first point to the breathing gas input port of the anesthetic gasifier unit. In some embodiments the flow generator unit is adapted to provide the rate of the flow of breathing gas to the anesthetic gasifier unit from the first point at a flow rate that is less than a bypass flow in the inspiratory patient gas delivery path passing the Y-piece from the inspiratory line to the expiatory line. Thus, a backflow of patient gas through the mainstream connection is advantageously prevented.

In some embodiments the aggregate further includes at least one gas source for generating a desired gas flow of a gas having a desired gas mixture to the gas input port in addition and to support the gas flow from the flow generator. This is for instance advantageous with low minute volumes, where a backflow from the patient side towards the input line of the aggregate is advantageously avoided.

In some embodiments the aggregate further has a selector valve that is provided to switch between operational modes of manual ventilation and automatic mechanical ventilation.

In embodiments, the aggregate has a control unit that regulates the desired concentration of the gasified anesthetic agent in the inspiratory patient gas delivery path. In some embodiments, the control unit is arranged to detect a connection of the anesthetic gasifier unit or aggregate to the inspiratory patient gas delivery path and a patient connected thereto. This detection is for instance based on a) a pressure data provided by a pressure sensor arranged to measure a pressure in the breathing gas input line, and/or a flow data of a flow in the inspiratory patient gas delivery path, and/or a capnogram data related to $CO_2$ fluctuations in the inspiratory patient gas delivery path. Further delivery of the anesthetic agent from the anesthetic gasifier unit is only allowed by the control unit when the connection is detected. This provides for improved safety.

In some embodiments the aggregate includes an anesthetic gas monitor for providing feedback input data for the regulation of the desired concentration of the gasified anesthetic agent in the inspiratory patient gas delivery path. Alternatively, or in addition, the regulation of the desired concentration of the gasified anesthetic agent in the inspiratory patient gas delivery path is based on a proportional ratio of a flow provided by the flow generator and a flow in the mainstream connection. In the latter embodiments a gas monitor may be omitted, which provides for an economically particularly attractive solution. When having an added gas monitor, safety is improved by two different, independent redundant concentration measurements of the anesthetic agent.

In embodiments the aggregate is an external module adapted to provide anesthesia capability to the breathing apparatus. The aggregate may be provided to add anesthesia volatile intensive capabilities to care ventilators at a low cost. The aggregate may be provided in a very compact manner.

According to a second aspect, a combination of a breathing apparatus (100) and the respiratory anesthetic aggregate according to the first aspect is provided connected thereto for providing substantially volume neutral delivery of the anesthetic agent to the patient.

In some embodiments, the aggregate works independently of the breathing apparatus when in operation. This provides for a convenient and safe solution.

In some embodiments the combination includes a transmission unit for transmission of information data to the respiratory anesthetic aggregate. Information data may include information data of a minute volume delivered to the inspiratory line from the breathing apparatus. Here, an anesthetic monitor may be omitted having the aforementioned advantages.

According to a third aspect, a computer program for processing by a computer, storable on a computer readable medium, is provided. The computer program comprising code segments for controlling delivery of an anesthetic agent from an anesthetic gasifier unit connected to an inspiratory line of a breathing apparatus in a sidestream configuration.

According to a fourth aspect, a method of supplying a substantially volume neutral fresh gas supply in a breathing apparatus is provided. The method comprises providing an anesthetic gasifier unit; connecting the anesthetic gasifier unit to an inspiratory line of a breathing apparatus in a sidestream configuration; and thus adding anesthesia capability to the breathing apparatus.

Further embodiments of the invention are defined in the dependent claims, wherein features for the second and subsequent aspects of the invention are as for the first aspect mutatis mutandis.

Delivery of anesthetic agent is thus made in a volume neutral manner. There is no need for a separate source of gas to the anesthetic gasifier unit. Breathing apparatuses based on the presently arranged and adapted anesthetic gasifier unit comprises in this manner less components and are cheaper to manufacture than traditional breathing apparatus having inhalational anesthesia capabilities provided by anesthetic gasifier units.

Some embodiments provide for improved measurement accuracy and delivery of gas components, volumes, pressures, etc., because the carrier gas is drawn from the breathing gas and supplied as a side stream flow to the anesthetic gasifier unit. The gas is returned to the breathing circuit with the gasified anesthetic agent added as fresh gas, without changing the volume of the returned gas significantly.

Some embodiments of the invention provide for improved patient safety. Anesthetic agent is for instance provided to the patient with high accuracy and correct measurements.

Some embodiments of the invention provide for improved user safety. Unintended spillage of anesthetic agent is for instance avoided.

Some embodiments of the invention provide for a delivery of clean, uncontaminated, carbon dioxide free gas to an anesthetic gasifier unit, thus improving safety. The anesthetic agent gasifier unit and related connected tubing needs not to be replaced between patients.

Some embodiments of the invention provide for a modular aggregate that may be used with existing intensive care ventilators, thus adding convenient anesthesia capabilities.

Some embodiments of the invention provide for a small, compact configuration of such modular aggregates.

Some embodiments of the invention provide for a detectable connection and/or disconnection to and/or from a breathing circuit of a breathing apparatus. Unintended leakage of anesthetic agent to the environment is thus avoided. Some embodiments of the invention provide for such detectable connection and/or disconnection to and/or from a breathing circuit of a breathing apparatus without the use of a specifically dedicated connection detector sensor.

Some embodiments of the invention provide for mechanical automated ventilation operation of a breathing apparatus with added anesthesia capability. Some embodiments of the invention provide in addition or alternatively for manual ventilation operation.

Embodiments of the invention provide for a delivery of anesthetic agents without droplets or aerosol build up, thus improving safety.

Embodiments of the invention provide for avoiding delivery of unvaporized liquid directly to a breathing circuit which is connected to a patient. Delivering liquid anesthetic to the patient could be a risk for the patient. Measurement of gasified anesthetic agent concentration and a feedback control thereof is made by means of units devised for measurement of gaseous component concentrations. In case a liquid portion of the anesthetic agent remains in the gas supplied to the patient, the measured agent concentration would be unreliable, and thus a risk for the patient may occur. Hence, embodiments of the invention prevent potentially dire consequences.

The device, aggregate, apparatus, system, method, and computer program product relate to administration of gaseous anesthetic agent and may be used with human beings or animals, in particular humans or animals by inhalational anesthesia and/or sedation.

It should be emphasized that the term "comprises/comprising" when used in this specification is taken to specify the presence of stated features, integers, steps or components but does not preclude the presence or addition of one or more other features, integers, steps, components or groups thereof.

DESCRIPTION OF THE PREFERRED EMBODIMENTS

Figure 1:
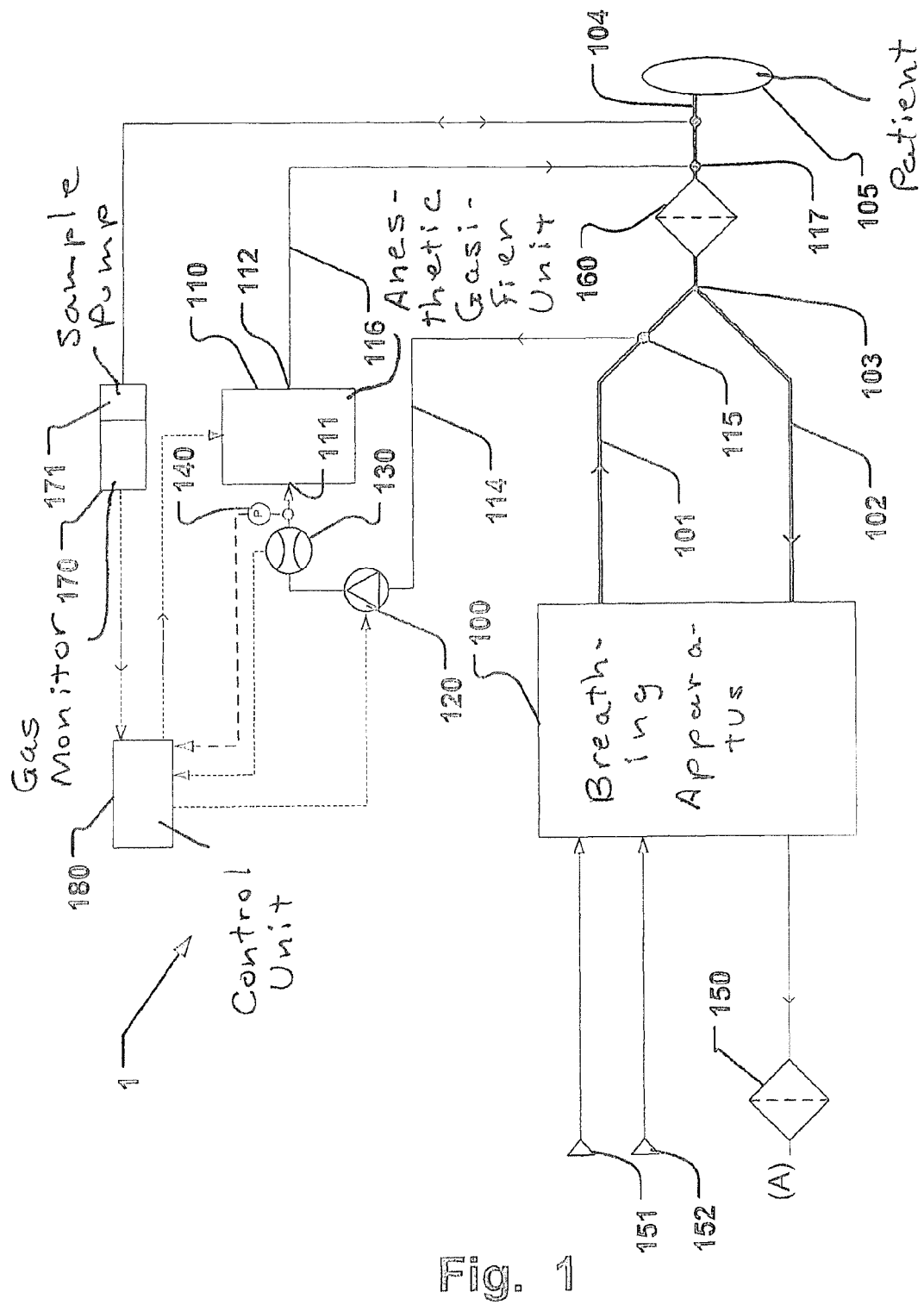
FIG. 1 is a schematic illustration of a breathing apparatus having connected thereto a modular respiratory anesthetic aggregate.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description describes embodiments applicable to a breathing apparatus and in particular to a respiratory ventilator in use connected to sources of pressurized gas. However, it will be appreciated that the invention is not limited to this application but may be applied to many other breathing apparatuses, including for example fan driven breathing apparatuses.

The embodiments describe circuit solutions for providing anesthesia with a breathing apparatus in form of an intensive care respiratory ventilator. The circuit solutions are provided as modular aggregates to be attached to the intensive care ventilator. The two embodiments are in particular well suited for different groups of patients. The first embodiment is in particular applicable to adult/pediatric patients, wherein the second embodiment is particularly advantageous for neonatal patients.

Now turning to the figures, a first embodiment is described with reference to FIG. 1. FIG. 1 is a schematic illustration of a breathing apparatus 100 having connected thereto a modular respiratory anesthetic aggregate 1. The breathing apparatus is for instance an intensive care ventilator.

The modular respiratory anesthetic aggregate 1 is devised for coupling to a breathing apparatus 100. The aggregate comprises an anesthetic gasifier unit 110 for providing a gasified anesthetic agent to the lungs of a patient 105. Furthermore, the aggregate 1 comprises the following components:
- a flow generator, here in form of a pump unit 120, provided for pumping breathing gas from a first point 115 to a breathing gas input port 111 of the anesthetic gasifier unit 110 via a breathing gas input line 114;
- a flow meter 130 and/or a flow indicator
- a circuit pressure sensor 140;
- an evac filter 150 in an exhaust of the breathing apparatus 100, to which gas is conveyed from an expiratory line 102;
- a anesthetic reflector unit 160, such as a carbon reflector;
- a gas monitor 170, such as an anesthetic gas monitor; the gas monitor 170 may have a sample pump 171;
- a control unit 180

In more detail, the anesthetic gasifier unit 110 is provided to gasify an anesthetic agent. The anesthetic gasifier unit 110 is for instance an anesthetic vaporizer, which may be based on various principles, such as thermal evaporation or injection of a liquid anesthetic agent. Some principles of quick regulability of delivered anesthetic agent may be advantageous for an automated feedback control of agent concentration delivered to the patient. A quick regulability is in particular provided by using an injection vaporizer as an anesthetic agent gasifier unit. The anesthetic gasifier unit 110 comprises the breathing gas input port 111 and a fresh gas output port 112. The fresh gas output port is arranged to provide the breathing gas supplied to the breathing gas input port 111 enriched with gasified anesthetic agent, namely as "fresh gas". The anesthetic gasifier unit 110 is devised to add a desired amount of an anesthetic agent to a gas flow of breathing gas, entering via the breathing gas input port 111 and leaving via the fresh gas output port 112, enriched with gasified anesthetic agent. This breathing gas, enriched with gasified anesthetic agent, is the aforementioned "fresh gas".

The breathing gas input port 111 is connected to the first point 115 in an inspiratory patient gas delivery path of a breathing apparatus 100 by means of the breathing gas input line 114. The inspiratory patient gas delivery path is part of a breathing circuit, connectable to a patient for providing assisted and/or controlled ventilation. The patient gas delivery path is for instance provided by gas conveying channels, such as hoses, flexible tubing, tubes, or the like, for providing a way of leakage free gas transport. The inspiratory patient gas delivery path comprises an inspiratory line 101, and a patient connection line 104 connected via a Y-piece 103. The inspiratory line is provided with gas from the breathing apparatus 100. The gas may be provided with a desired oxygen concentration, blended from suitable gas sources for $O_2$ 151 and Air 152 connected to the breathing apparatus 100, as illustrated. Other embodiments may comprise gas sources for other gases, such as nitrous oxide, heliox.

Breathing gas input line 114 is arranged to provide clean input of breathing gas to gasifier 110 as the reflector 160 works as a filter. Breathing gas in input line 114 is further free of expired $CO_2$ since all expired gas is passed to evac during the expiratory phase via the Y-piece.

Breathing gas input line 114 is for instance provided as a flexible tubing. Alternatively, or in addition, breathing gas input line 114 may at least partly comprise rigid gas conveying channels, which may be part of a compact modular aggregate connected to existing patient tubing of a breathing apparatus.

The fresh gas output port 112 is connected to a second point 117 in the inspiratory patient gas delivery path via a fresh gas output line 116. The second point 117 is arranged downstream the first point 115 in the inspiratory patient gas delivery path. Moreover, the inspiratory patient gas delivery path is connected via a mainstream connection between the first point 115 and the second point 117. Breathing gas is in use provided in the mainstream flow. Thus, the anesthetic gasifier unit 110 is in use connected in a sidestream configuration to the inspiratory patient gas delivery path for adding the gasified anesthetic agent in a desired amount or concentration to the inspiratory patient gas delivery path at the second point 117.

Fresh gas output line 116 is for instance provided as a flexible tubing. Alternatively, or in addition, output line 116 may at least partly comprise rigid gas conveying channels, which may be part of the compact modular aggregate.

Figure 2:
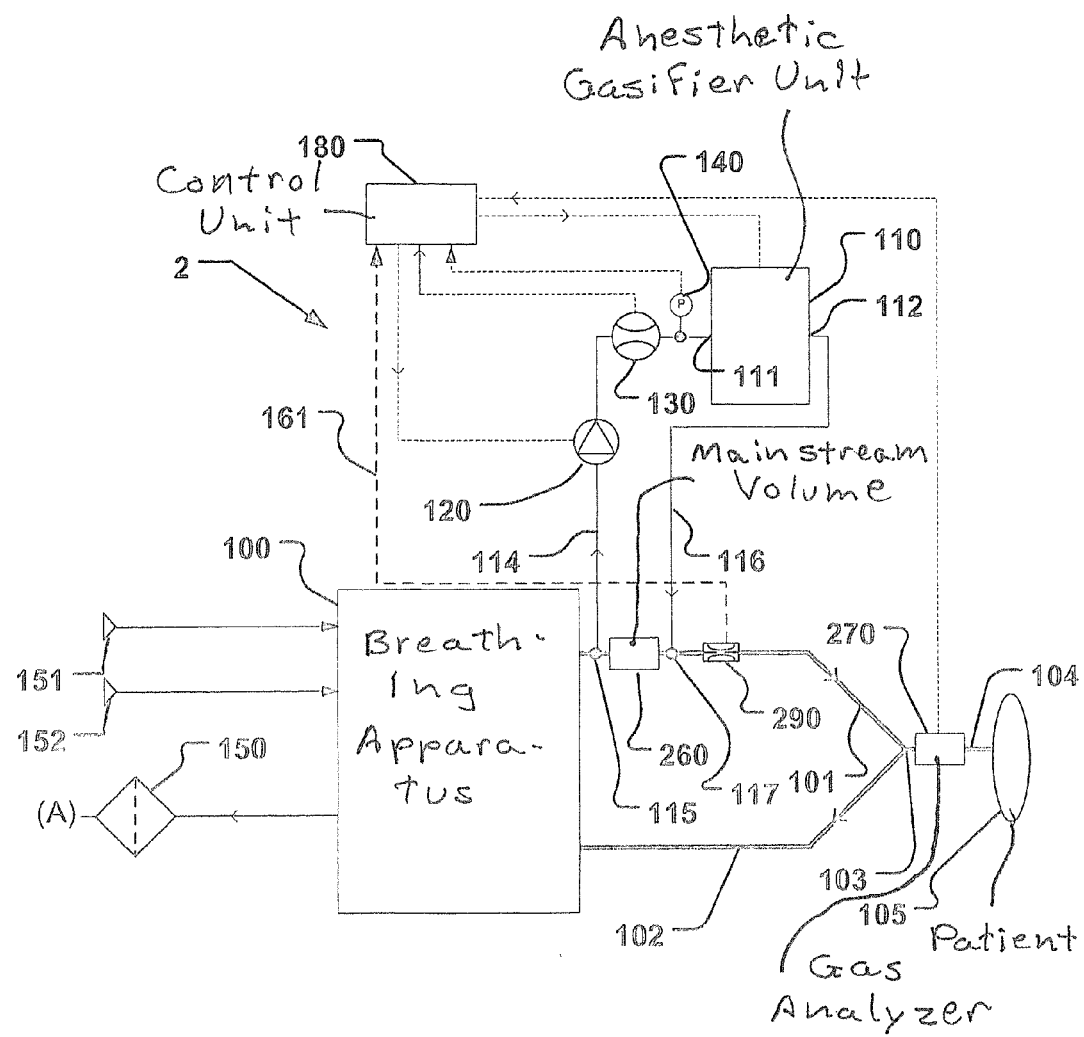
FIG. 2 is a schematic illustration of a breathing apparatus having connected thereto another modular respiratory anesthetic aggregate.

The aggregate 1 is in particular applicable to adult or pediatric patients. Another aggregate 2, which is in particular applicable to neonatal patients, is illustrated in FIG. 2 and described in more detail below.

The pump unit 120 draws gas from the inspiratory line 101 of the breathing apparatus 100. The flow rate of gas generated by the pump unit 120 is chosen to be lower than a gas flow in the inspiratory line 101 of breathing apparatus 100. This condition is important in order to avoid exposure to anesthetic agents and patient gas for the internal components of the device, which could occur by a backflow through line 101 into the breathing apparatus 100, if the condition was not met. This condition may for instance be fulfilled by choosing the pump flow rate to be lower than a bias flow in the inspiratory line 101 continuously flowing to the expiratory line 102 at the Y-piece 103. Alternatively, or in addition, the pump flow may be controlled in dependence of the actual gas flow in the inspiratory line 101, namely at the first point 115.

The gas flow in the inspiratory line 101 is in the embodiment provided to the aggregate 1 from the breathing apparatus 100. The pump flow rate is measured by means of flow meter 130 arranged in series with the pump unit 120. A pump flow rate signal is provided to the control unit 180 for a feedback regulation of the pump flow rate.

The pump flow rate may be controlled automatically by the control unit 180. Alternatively, or in addition, a target pump flow rate may be set manually by a user. Alternatively, the pump 120 may be set to a fixed pump flow rate.

The pump flow rate is preferably low in comparison to the main stream flow rate, as the anesthetic gasifier is capable of providing high concentrations of gasified anesthetic agent. In this manner, the modular embodiments of the modular respiratory anesthetic aggregate may be provided in a very compact arrangement. In addition, an additional flow of gas may be provided to breathing gas input port 111, as described below with reference to FIGS. 6 and 7.

The main purpose of the pressure sensor 140 is to monitor that the device is connected properly and that the patient is being ventilated, which will be indicated by a fluctuating pressure. If the breathing apparatus is set in standby mode the pressure sensor 140 will detect that the pressure is at a constant level and necessary actions will be taken to turn off the carrier gas flow and the vaporizer. Also, upon disconnecting the breathing circuit, e.g. by disconnecting the tubing 101 or 102 or the Y-piece 103, the pressure will substantially drop continuously to ambient pressure. Thus, the anesthetic gasifier unit 110 may be deactivated and any distribution thereof to the ambient environment is effectively prevented. The pressure sensor 140 may also be used to monitor leakage in the carrier gas line.

The gas then continues flowing trough the anesthetic gasifier unit 110 where the anesthetic agent is added at a rate set directly or indirectly by the user, e.g. as a concentration or dosage of anesthetic agent to be delivered to the patient, as described below.

The gas flow then continues to the patient side of the reflector 160, where it is added to the patient's inhaled and exhaled gas at the second point 117. The anesthetic reflector is for instance a carbon reflector that acts as an adsorbing and desorbing reflector for the anesthetic components in the exhaled and inhaled gases. Anesthetic reflectors are for instance described in U.S. Pat. Nos. 5,044,361 or 5,471,979, which are incorporated herein by reference in their entirety for all purposes.

The anesthetic reflector 160 may be provided with an activatable bypass, such as disclosed in WO 2007/110112 of the same applicant as the present application, which is incorporated herein by reference in its entirety for all purposes. The bypass may be activated for wake-up or ending anesthesia and rinsing of the breathing circuit from gaseous anesthetic agent.

A concentration of gasified anesthetic agent delivered to the patient 105 is measured, for instance by means of side stream gas monitor 170. Alternatively, the gas monitor 170 may be a mainstream sensor based gas monitor without the need for a side stream sample pump, see FIG. 2. The gas monitor may measure further gas, such as oxygen, nitrous oxide, carbon dioxide, etc.

A detection of carbon dioxide in capnographic measurement provides for detection of a patient 105 connected to the breathing circuit. Delivery of anesthetic agent may be commenced or discontinued depending on this condition and other conditions, such as pressure fluctuations detected by the pressure sensor 140, as described above. For safety reasons, the delivery of anesthetic agent from the unit 110 may be stopped or not initiated by the control unit 180, e.g. when a disconnection from the breathing circuit, the breathing apparatus 100, or the patient 105 is detected. This applies to all embodiments providing this detectability. Detection may be based on a detection of $CO_2$, pressure fluctuations, etc.

A regulation of the concentration of gasified anesthetic agent delivered to the patient 105 may be provided in various ways. The concentration to the patient depends on parameters including the minute ventilation, the pump gas flow trough the anesthetic gasifier unit 110, the anesthetic gasifier unit 110 dosing rate, efficiency of the reflector 160, and the patient uptake of the anesthetic agent. Specific control algorithms for regulating patient agent concentration may be tailor made for specific requirements.

For a regulation of the concentration of gasified anesthetic agent delivered to the patient 105, the user may set an absolute or relative concentration of gasified anesthetic agent in the gas flow leaving the anesthetic gasifier unit 110, and then the user observes the resulting concentration to the patient with the gas monitor 170, e.g. on a display.

Thus, the user sets the inspired inhalation agent concentration according to the reading of the gas monitor. In the case of a faulty gas monitor it is for safety reasons necessary that the inspired inhalation agent concentration does not can reach harmful levels. There are different methods to prevent this, for instance:

The gas analyzer module receives information about the minute volume from the breathing apparatus. This can be provided by wired or wireless communication. The control unit 180 and program product therein then automatically limits the maximum vaporizer setting in respect to the minute ventilation in order to limit the inspired inhalation agent concentration.

The user sets the maximum vaporizer setting with respect to the minute ventilation out of a nomogram. No data communication with the ventilator is needed in this case.

Alternatively, the regulation of the concentration of gasified anesthetic agent delivered to the patient 105 may be automatically controlled in a feedback loop via the control unit 180. A user provided target value for the desired concentration of gasified anesthetic agent is thus delivered to the patient 105, wherein the user enters the target value via a suitable user interface. The control unit 180 applies then suitable algorithms controlling the pump flow rate of pump 120 and the amount of anesthetic agent added by anesthetic gasifier unit 110 to deliver a concentration corresponding to the desired target value. The gas monitor 170 provides a measured feedback value of the control loop via control unit 180. A display (not shown) may show the concentration of gasified anesthetic agent delivered to the patient 105.

For safety reasons, a second gas analyzer may be provided for redundant measurement of gasified anesthetic agent, such as disclosed in international application PCT/EP2007/062357, of the same applicant as the present application, which is incorporated herein by reference in its entirety for all purposes.

Another embodiment will now be described with reference to FIG. 2. In FIG. 2 a breathing apparatus 100 is schematically shown having connected thereto a modular respiratory anesthetic aggregate 2.

The embodiment shown in FIG. 2 is particularly applicable with neonatal patients where the tidal volumes are small and the need for reflecting the anesthetic gases is small. The aggregate 2 comprises the same circuitry as the previous embodiment, except the anesthetic reflector. However, the first point 115 and the second point 117 are both arranged in the inspiratory line 101 upstream of the Y-piece of the breathing apparatus 100. The first point 115 and the second point 117 are separated by a mainstream volume 260. The mainstream volume 260 is provided as a buffer in order to achieve an even concentration to the patient 105. Furthermore, the volume 260 prevents a backflow of anesthetic agent from point 117 into the apparatus 100. As the present embodiment does not comprise a reflector, and thereby the circuit does not add any dead space to the patient circuit, this embodiment is particularly advantageous for the neonatal patient category. The embodiment may also be used for pediatric or adult patients.

A mainstream gas sensor 270 provides measurement of gasified anesthetic agent concentration. Alternatively, a sidestream gas analyzer, as described with reference to FIG. 1, may be used.

Alternatively, the gas analyzer 270 may be omitted. In this case, a control of concentration of gasified anesthetic agent may be provided by a proportional delivery thereof. This delivery is made at a controlled anesthetic agent delivery flow rate. Furthermore, the flow meter 290 provides a measure for the total patient flow. Hence, based on the agent delivery flow rate and the total flow rate, as well as the concentration of gasified anesthetic agent in the agent delivery flow, the concentration of gasified anesthetic delivered to the patient is known and regulatable without the use of a gas analyzer, which provides for a specifically reduced cost solution. The concentration of gasified anesthetic delivered to the patient is for instance known by calculations based on the aforementioned parameters. Such calculations are in particular provided with high precision by using an injection vaporizer as an anesthetic agent gasifier unit. Hence, the amount, and thus the dose, of injected anesthetic agent is very precisely known, whereby the aforementioned calculation is provided in an advantageous manner with regard to patient safety and/or apparatus cost. For further safety reasons, a gas analyzer may be provided for redundant measurement of gasified anesthetic delivered to the patient.

Figure 7:
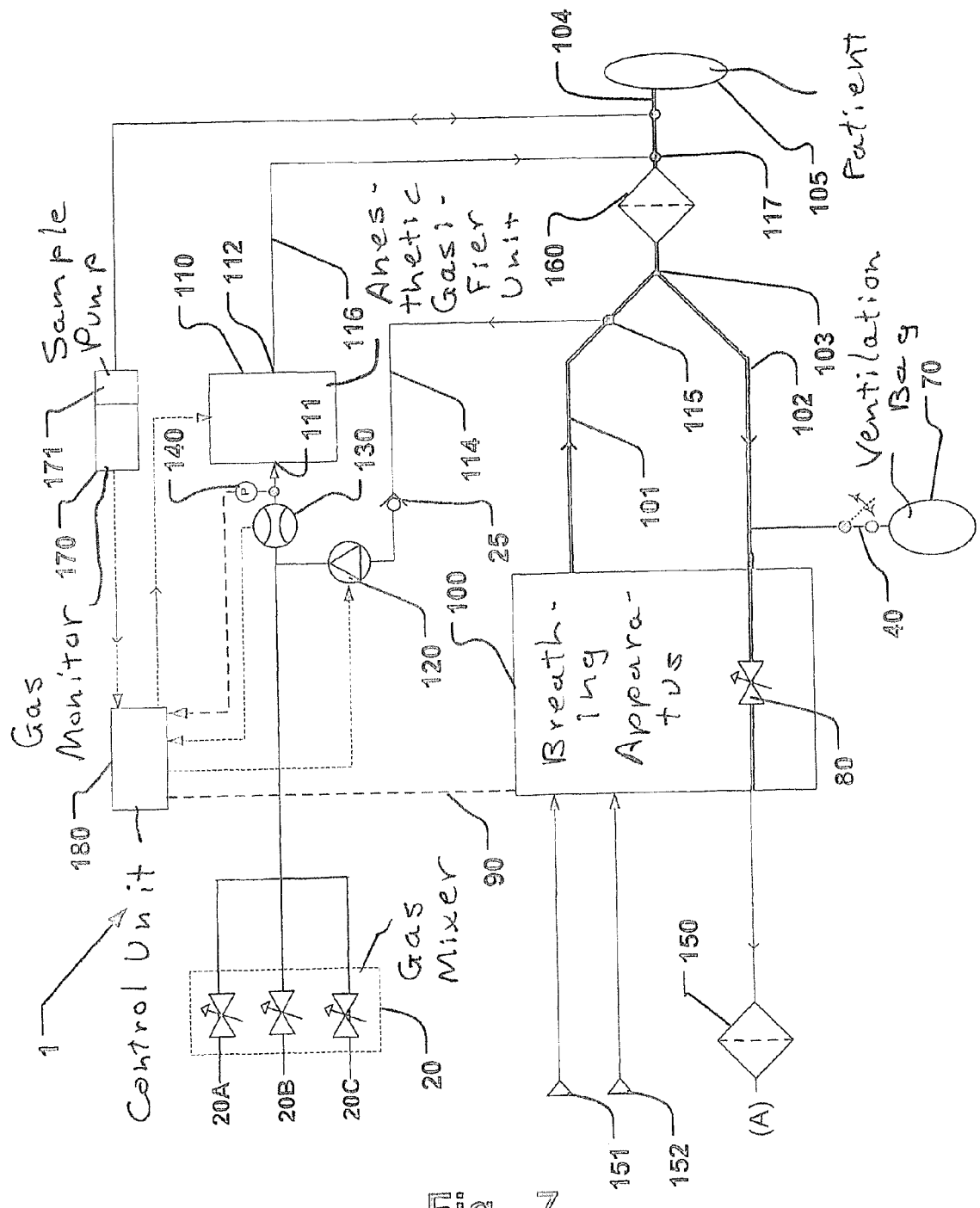

A flow meter 290 is provided in order to supply information about the patient minute ventilation, in case the concentration to the patient is automatically controlled. The flow meter 290 is connected to control unit 180 via a communication link 161 that may be wired or wireless. Alternatively, the minute ventilation information may also be transferred from the breathing apparatus 100 via a communication link 90 as shown in FIG. 7. The communication link may be wired or wireless.

Figure 3:
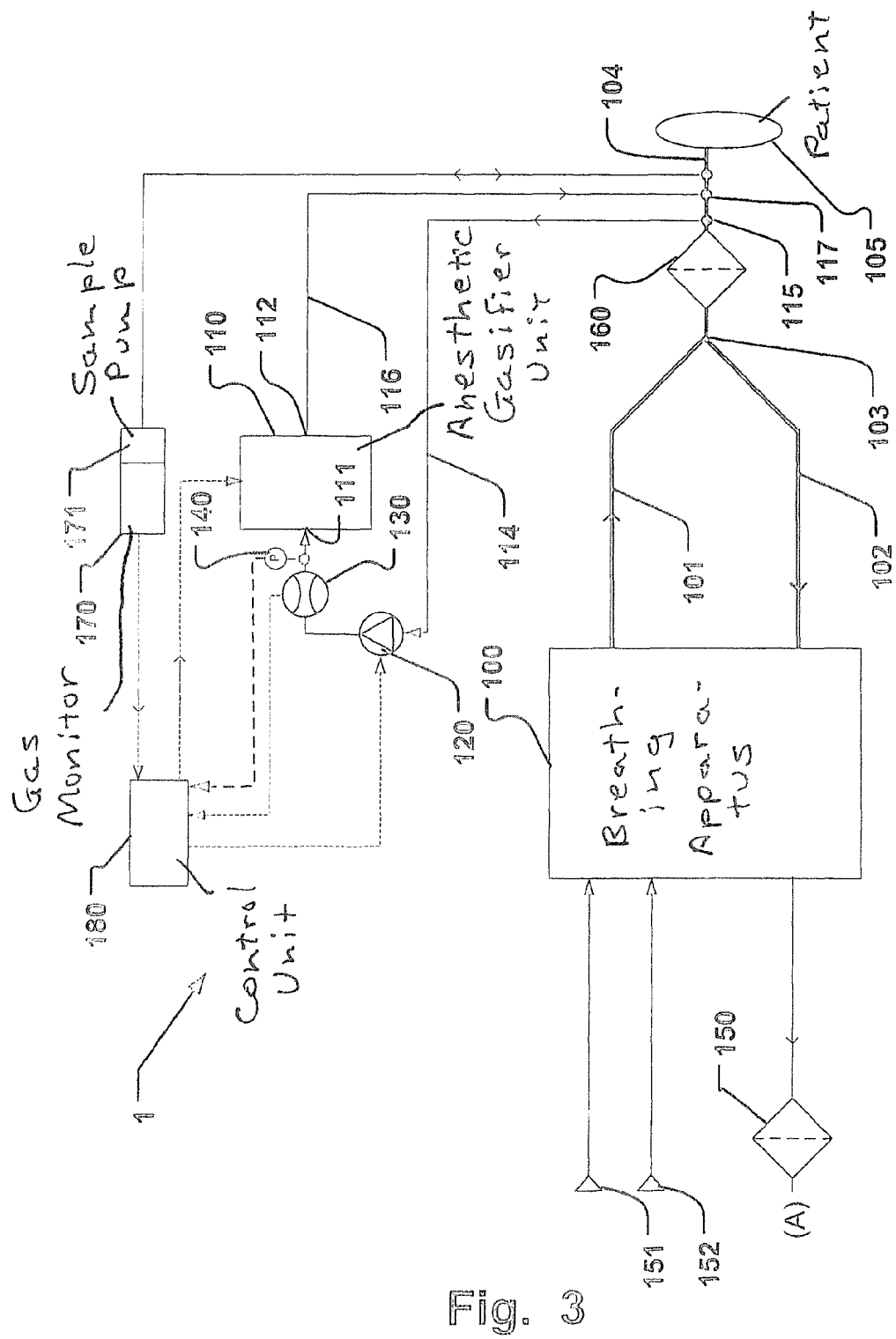
FIG. 3 is a schematic illustration of a breathing apparatus having connected thereto the modular respiratory anesthetic aggregate of FIG. 1 connected to the apparatus in another configuration.

With reference to FIG. 3, a further embodiment is illustrated. The breathing apparatus 10 has connected thereto the modular respiratory anesthetic aggregate 1 of FIG. 1. However, the configuration of the first point 115 differs from the arrangement shown in FIG. 1. The first point 115 is arranged in the patient line 104 downstream the anesthetic reflector 160, seen in inspiratory direction. Here, the feed flow of gas in line 114 comprises patient contaminated gas, anesthetic agent, water vapor, as well as $CO_2$ expired by the patient. However, this arrangement may in some practical implementation be preferred. The arrangement in FIG. 3 provides the same advantages of connection detectability, volume neutral delivery of anesthetic agent, etc.

In some embodiments the flow controller, e.g. in form of a pump may be integrated into a gasifier unit. The pump may be a micro pump allowing for particular miniaturization of such embodiments.

In some embodiments the agent gasifier unit may be micro machining technology based allowing for particular miniaturization of such embodiments.

In the illustrated embodiments, an EVAC filter 150 is placed in the expiratory outlet of the breathing apparatus 100 to reduce the amount of halogenated carbons exhausted into the ambient air (A). The EVAC filter 150 contains for instance activated carbon as a filter material. Alternatively, or in addition, the exhaust of the breathing apparatus 100 may be connected to a vacuum system for handling of the exhaust gases. In addition, the evac filter may be combined with a germ or bacteria filter preventing spreading of infection carriers and other pathogenic matter to the ambient environment or the vacuum system.

Figure 4:
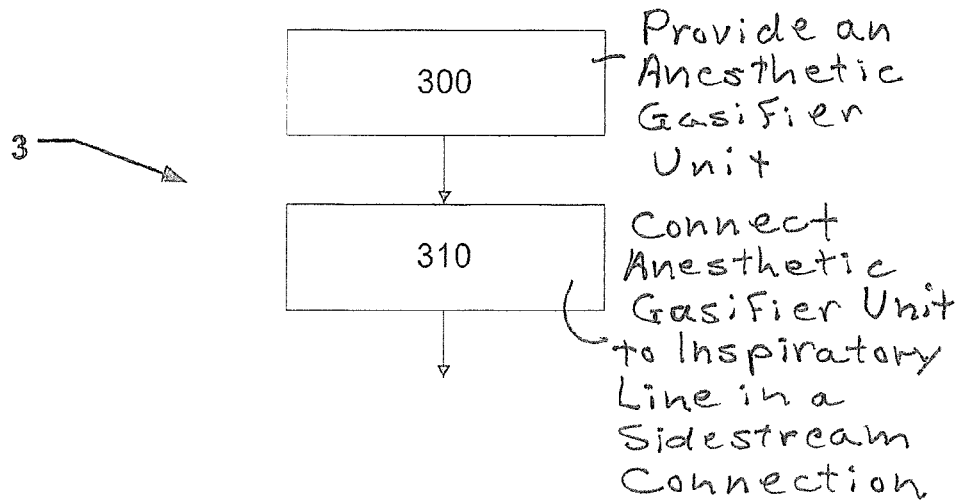
FIG. 4 is a schematic illustration of a method of sidestream delivery of a gasified anesthetic agent.

FIG. 4 is a schematic illustration of a method 3 of sidestream delivery of a gasified anesthetic agent. The method 3 is a method of supplying a substantially volume neutral fresh gas supply in a breathing apparatus. The method 3 comprises providing 300 an anesthetic gasifier unit 110; connecting 310 the anesthetic gasifier unit 110 to an inspiratory line 101 of a breathing apparatus 100 in a sidestream configuration; and thus adding anesthesia capability to the breathing apparatus 100.

The providing of the anesthetic gasifier unit 110 comprises providing an anesthetic gasifier unit adapted to gasify an anesthetic agent, comprising a breathing gas input port and a fresh gas output port. The providing of the sidestream configuration comprises connecting the breathing gas input port to a first point in an inspiratory patient gas delivery path of the breathing apparatus by means of a breathing gas input line, and connecting the fresh gas output port to a second point in the inspiratory patient gas delivery path via a fresh gas output line. The second point is arranged downstream the first point in the inspiratory patient gas delivery path, and the inspiratory patient gas delivery path is connected via a mainstream connection between the first and second point, whereby the anesthetic gasifier unit is connected in the sidestream configuration to the inspiratory patient gas delivery path for adding the gasified anesthetic agent in a desired concentration to the inspiratory patient gas delivery path at the second point.

In an embodiment, the method further comprises coupling a modular respiratory anesthetic aggregate to the breathing apparatus, wherein the aggregate comprises an embodiment of the anesthetic gasifier unit 110 described above, and a flow generator unit for providing a flow of breathing gas from the first point to the breathing gas input port of the anesthetic gasifier unit.

The method further comprises providing a feedback control of the anesthetic agent delivery.

Figure 5:
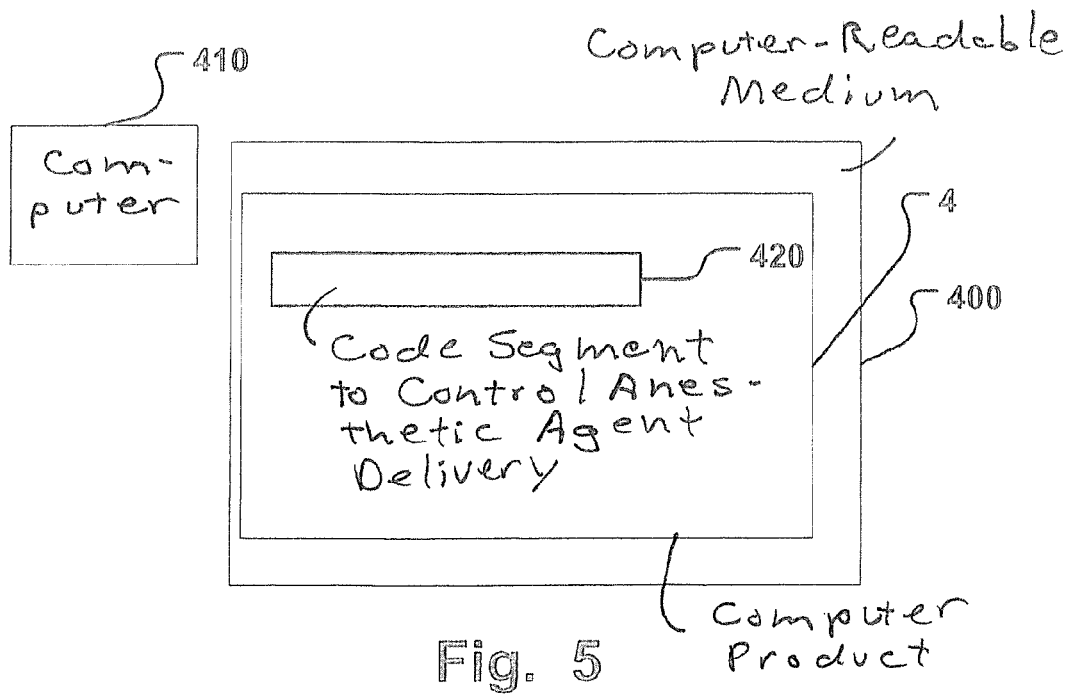
FIG. 5 is a schematic illustration of a computer program product for controlling sidestream delivery of a gasified anesthetic agent.

FIG. 5 is a schematic illustration of computer product 4 for controlling sidestream delivery of a gasified anesthetic agent. The computer program is devised for processing by a computer 410, such as the control unit 180, and is stored on a computer readable medium 400, such as a memory, an optical data storage unit, a magnetic data storage unit, etc. The computer program comprises a code segment 420 for controlling delivery of an anesthetic agent from an anesthetic gasifier unit 110 connected to an inspiratory line 101 of a breathing apparatus 100 in a sidestream configuration. The computer program preferably is provided to perform the above described method.

Figure 6:
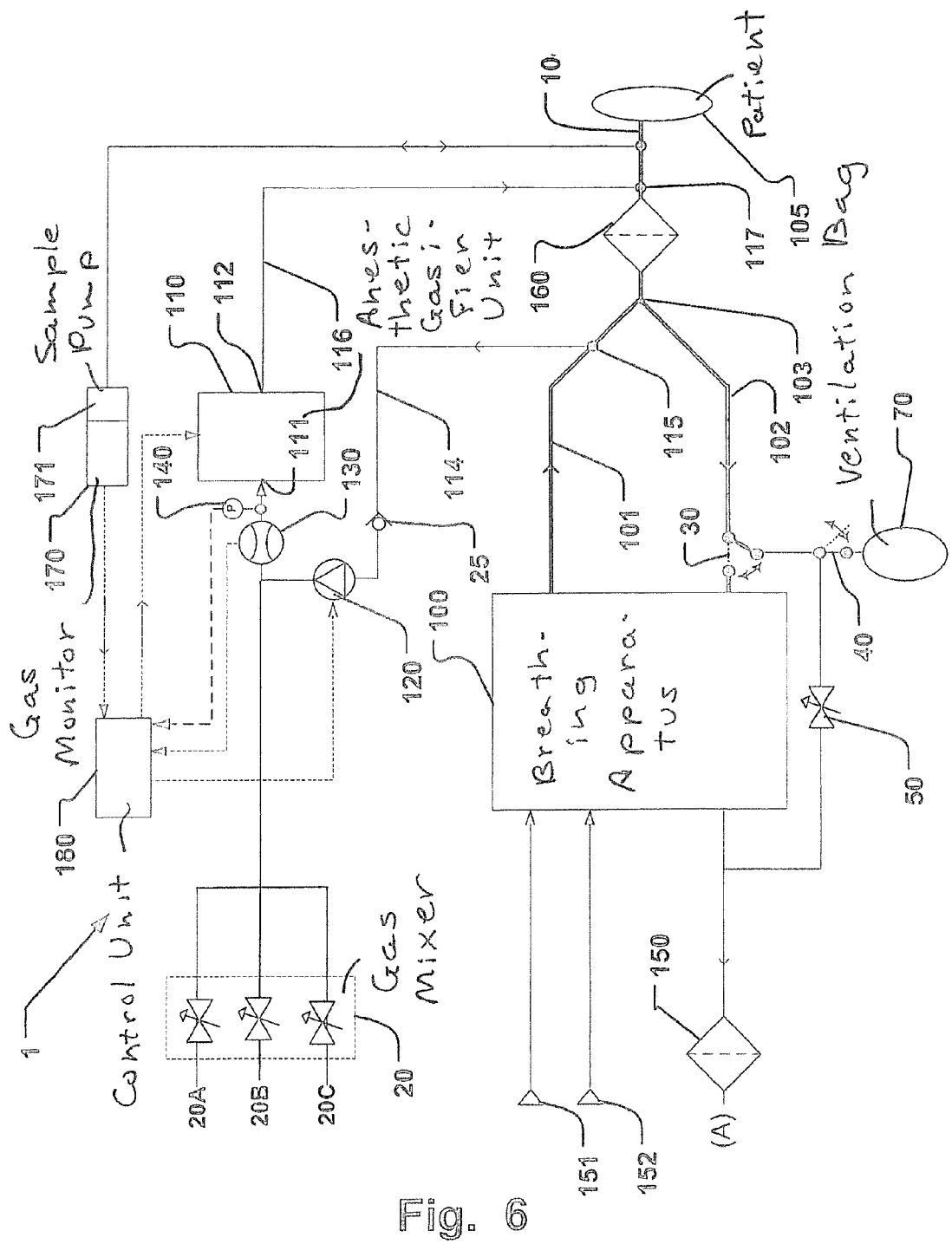
FIGS. 6 and 7 are schematic illustrations of two breathing apparatuses having connected thereto a modular respiratory anesthetic aggregate having a gas mixer and allowing for manual ventilation.

FIGS. 6 and 7 are schematic illustrations of two breathing apparatuses having connected thereto a modular respiratory anesthetic aggregate allowing for manual ventilation.

With reference to FIG. 6, a further embodiment is illustrated. FIG. 6 is a schematic illustration of a breathing apparatus 100 having connected thereto a modular respiratory anesthetic aggregate 1.

A gas mixer 20 is provided for generating a desired gas flow of a gas having a desired gas mixture from gas sources for $N_2O$ 20A, $O_2$ 20B, and Air 20C. The gas mixer 20 may be mechanical and/or electrical.

Selector valve 30 is provided to switch between manual ventilation and automatic mechanical ventilation.

Selector valve 40 is provided to connect a manual ventilation bag 70. The selector valve 40 may be omitted in the embodiment described with reference to FIG. 6.

In FIG. 6, the valves 30, 40 are shown in the position for manual ventilation by means of the manual ventilation bag 70.

During manual ventilation operation mode, the pump 120 is switched off. A check valve 25 is provided to prevent a gas flow through line 114 to the first point 115. The pump 120 may be manually switched off. Alternatively, the pump 120 may be automatically switched off, e.g. by control unit 180 or a software thereof. The automatic switching off of pump 120 is synchronized with the activation of the manual ventilation mode. Synchronization may be based on detecting activation of the selector valve 30 and/or 40 to manual mode. Alternatively, or in addition, synchronization may be based on a signal provided by valve 30 and/or valve 40, e.g. one or more of a current for activating such valve, a mechanical switch activated by the valve in a certain mode of operation or during transition between such modes, or a suitable sensor detecting the mode of operation.

An external gas may be provided in other embodiments than those illustrated in FIGS. 6 and 7. For instance when added to the embodiment described with reference to FIG. 2, an embodiment that is particularly adapted for neonatal use is provided. This design having an external gas mixer 20 and a selectable manual ventilation mode is also providable in embodiments for ventilation of patients having small lungs, such as neonatal or pediatric patients. The enhanced capabilities and advantages of the external mixer, and manual ventilation, may thus be added to embodiments described herein.

During manual ventilation operation mode, a constant gas flow is provided by gas mixer 20. The flow rate of this gas flow is set to a desired value, preferably user selectable. An adjustable pressure limit valve 50, commonly called APL valve is provided. The APL valve 50 has the function to limit the pressure of breathing gas that can occur in the breathing circuit during manual ventilation.

With reference to FIG. 7, a further embodiment is illustrated. FIG. 7 is a schematic illustration of a breathing apparatus 100 having connected thereto a modular respiratory anesthetic aggregate 1.

Alternatively to the embodiment as described with reference to FIG. 6, a PEEP/APL valve 80 is provided to either control a positive end expiratory pressure (PEEP) level during mechanical ventilation by ventilator 100, or for providing an APL valve function during manual ventilation provided by means of the manual ventilation bag 70. Such a PEEP/APL valve 80 is for instance described in international patent application WO2007/071756 of the same applicant as the present application, which is incorporated herein by reference for all purposes.

In FIG. 7, the valve 40 is shown in the position for manual ventilation by means of the manual ventilation bag 70. Control unit 180 and ventilator 100 communicate with each other, as indicated by the dashed line 90. This communication provides for an automated switching between manual and mechanical ventilation.

During mechanical ventilation, the valve 80 functions as an expiratory valve regulating a desired PEEP during the expiratory phase of mechanical ventilation. During the inspiratory phase, the valve 80 may be controlled to provide for a desired bypass flow through lines 101 and 102, e.g. for inhalational flow triggering. Alternatively, the valve 80 may be closed during the inspiratory phase.

During manual ventilation, the valve 80 functions as an APL valve to limit the pressure of breathing gas that can occur in the breathing circuit.

An external gas flow, as provided by the gas mixer 20, may be used to increase the gas flow through the vaporizer 110 during mechanical ventilation as provided by the ventilator 100. This may for instance be advantageous in operational cases where the gas flow provided by the pump 120 is not sufficient. This may for instance be the case when a high concentration of anesthetic agent is to be supplied to a patient requiring a high minute volume. A gas flow from mixer 20 then provides for an additional gas flow through the vaporizer 110. Due to the additional gas flow provided by an external gas source, the gas flow through line 116 is not volume neutral.

The present invention has been described above with reference to specific embodiments. However, other embodiments than the above described are equally possible within the scope of the invention. The different features and steps of the invention may be combined in other combinations than those described. The scope of the invention is only limited by the appended patent claims.

We claim as our invention:

1. A respiratory anesthetic aggregate comprising:
    a breathing apparatus comprising an inspiratory patient gas delivery path;
    an anesthetic gasifier unit that gasifies an anesthetic agent to enrich breathing gas free of expired $CO_2$ with gasified anesthetic agent, said gasifier unit comprising a breathing gas input port and a fresh gas output port;
    said breathing gas input port being connected to a first point in said inspiratory patient gas delivery path downstream of said breathing apparatus by a breathing gas input line that supplies an amount of breathing gas free of expired $CO_2$ to the anesthetic gasifier;
    said fresh gas output port being connected to a second point in said inspiratory patient gas delivery path via a fresh gas output line;
    said second point being downstream of said first point in said inspiratory patient gas delivery path and downstream of said breathing apparatus, and said inspiratory patient gas delivery path being connected via a mainstream connection of breathing gas between said first point and said second point;
    said anesthetic gasifier unit being connected in a sidestream configuration to said inspiratory patient gas delivery path, between said first point and said second point, to add said gasified anesthetic agent in a desired concentration to said inspiratory patient gas delivery path at said second point, said sidestream connection between said first point and said second point insuring that the added gasified anesthetic agent does not increase said amount;
    a flow generator unit that provides a flow of breathing gas from said first point to said breathing gas input port of said anesthetic gasifier unit; and
    said flow generator unit being configured to provide a rate of said flow of breathing gas to said anesthetic gasifier unit from said first point that is less than a flow of gas supplied through said inspiratory patient gas delivery path by said breathing apparatus to said first point, to make a flow of gas via said mainstream connection toward said patient larger than zero when said flow generator unit provides a flow of breathing gas from said first point to said breathing gas input port of said anesthetic gasifier unit.

2. The aggregate according to claim 1, wherein said anesthetic gasifier unit supplies said gasified anesthetic agent with a breathing gas supply from said first point, and said anesthetic gasifier unit provides said gasified anesthetic agent at said second point as a fresh gas output in a volume neutral manner.

3. The aggregate according to claim 1 comprising a Y-piece, and wherein said first point is located upstream of said Y-piece and is connected to said inspiratory patient gas delivery path via said Y-piece and an inspiratory line, and wherein said anesthetic gasifier unit is provided with gas at said breathing gas input port that is $CO_2$-free and uncontaminated by said patient.

4. The aggregate according to claim 3, wherein said second point is connected to a common inspiration and expiration patient connection line of said inspiratory patient gas delivery path downstream of said Y-piece.

5. The aggregate according to claim 3 wherein said second point is connected to said inspiratory line.

6. The aggregate according to claim 1, comprising a control unit, a sidestream flow meter, and a gas analyzer for feedback control of gasified anesthetic agent delivered to a patient connected to the breathing apparatus.

7. The aggregate according to claim 1, comprising an anesthetic reflector unit or a mainstream volume arranged in said mainstream connection between said first point and said second point.

8. The aggregate according to claim 1, wherein said first point is located at a distance from said second point and said inspiratory patient gas delivery path is comprised in a breathing circuit connected to said breathing apparatus, and comprising:
- a Y-piece;
- a reflector located between said first point and said second point; and
- said first point is located upstream of said Y-piece and is connected to said inspiratory patient gas delivery path via said Y-piece and an inspiratory line, and said second point is connected to a patient connection line downstream of said Y-piece.

9. The aggregate according to claim 8, wherein said flow generator unit is configured to provide said rate of said flow of breathing gas to said anesthetic gasifier unit from said first point at a flow rate that is less than a bypass flow in said inspiratory patient gas delivery path passing said Y-piece from said inspiratory line to said expiatory line.

10. The aggregate according to claim 1, wherein said first point is located at a distance from said second point and said inspiratory patient gas delivery path is comprised in a breathing circuit connected to said breathing apparatus, and comprising:
- a Y-piece;
- a mainstream volume between said first point and said second point and both said first point and said second point are connected to an inspiratory line of said inspiratory patient gas delivery path upstream of said Y-piece.

11. The aggregate according to claim 1, wherein said first point is located at a distance from said second point and said inspiratory patient gas delivery path is comprised in a breathing circuit connected to said breathing apparatus, and comprising:
- a Y-piece;
- a reflector is located between said first point and said second point; and
- said first point is located upstream of said Y-piece and is connected to said inspiratory patient gas delivery path via said Y-piece and an inspiratory line, and said second point is connected to a patient connection line downstream of said Y-piece.

12. The aggregate according to claim 1, comprising at least one gas source selected from the group consisting of gas sources for $N_2O$, $O_2$, and atmospheric air connected to a gas mixer, said at least one gas source generating and providing a desired gas flow of a gas having a desired gas mixture to said gas input port in addition and to support said gas flow from said flow generator.

13. The aggregate according to claim 1, comprising a selector valve that switches between operational modes of manual ventilation and automatic mechanical ventilation.

14. The aggregate according to claim 1, wherein said gasifier unit is configured to regulate said desired concentration of said gasified anesthetic agent in said inspiratory patient gas delivery path based on a proportional ratio of a flow provided by said flow generator and a flow in said mainstream connection.

15. The aggregate according to claim 1, formed as an external module adapted to provide anesthesia capability to said breathing apparatus.

16. A combination comprising:
- a breathing apparatus;
- a respiratory anesthetic aggregate coupled to said breathing apparatus, said aggregate comprising an anesthetic gasifier unit that gasifies an anesthetic agent, said gasifier unit comprising a breathing gas input port and a fresh gas output port;
- a Y-piece;
- said breathing gas input port being connected to a first point in an inspiratory patient gas delivery path downstream of said breathing apparatus by a breathing gas input line;
- said first point being located upstream of said Y-piece, and wherein said anesthetic gasifier unit is provided with gas at said breathing gas input port that is CO2-free and uncontaminated by a patient;
- said fresh gas output port being connected to a second point in said inspiratory patient gas delivery path via a fresh gas output line;
- said second point being located downstream of said first point in said inspiratory patient gas delivery path, and said inspiratory patient gas delivery path being connected via a mainstream connection of breathing gas between said first point and said second point;
- said anesthetic gasifier unit being a module that is selectively connected in a sidestream configuration to said inspiratory patient gas delivery path, between said first point and said second point, to add said gasified anesthetic agent in a desired concentration to said inspiratory patient gas delivery path at said second point, said sidestream connection between said first point and said second point insuring that the added gasified anesthetic agent does not increase said amount;
- a flow generator unit that provides a flow of breathing gas from said first point to said breathing gas input port of said anesthetic gasifier unit; and
- said flow generator unit being configured to provide a rate of said flow of breathing gas to said anesthetic gasifier unit from said first point that is less than a flow of gas supplied through said inspiratory patient gas delivery path by said breathing apparatus to said first point, to make a flow of gas via said mainstream connection toward said patient larger than zero when said flow generator unit provides a flow of breathing gas from said first point to said breathing gas input port of said anesthetic gasifier unit.

17. The combination according to claim 16, comprising a transmission unit for transmission of information data to said respiratory anesthetic aggregate, said information data comprising information data of a minute volume delivered to said inspiratory line from said breathing apparatus.

18. The combination according to claim 16, wherein said anesthetic gasifier unit is arranged in a sidestream configuration at an inspiratory limb of said breathing apparatus.

19. The combination according to claim 16, wherein said respiratory anesthetic aggregate is arranged externally at said breathing apparatus in a modular configuration.

20. The combination according to claim 16, wherein said first point is located at a distance from said second point and said inspiratory patient gas delivery path is comprised in a breathing circuit connected to said breathing apparatus, and comprising:
- a reflector located between said first point and said second point;
- wherein said first point is located upstream of said Y-piece and is connected to said inspiratory patient gas delivery path via said Y-piece and an inspiratory line, and said second point is connected to a patient connection line downstream of said Y-piece.

21. The combination according to claim 16, wherein said second point is connected to a common inspiration and expiration patient connection line of said inspiratory patient gas delivery path downstream of said Y-piece.

22. A respiratory anesthetic aggregate comprising:
- a breathing apparatus;

coupled to said breathing apparatus, an anesthetic gasifier unit that gasifies an anesthetic agent, said gasifier unit comprising a breathing gas input port and a fresh gas output port;

said breathing gas input port being connected to a first point in an inspiratory patient gas delivery path downstream of said breathing apparatus by a breathing gas input line;

said fresh gas output port being adapted for connection to a second point in said inspiratory patient gas delivery path via a fresh gas output line;

said second point downstream said first point in said inspiratory patient gas delivery path, and said inspiratory patient gas delivery path is connected via a mainstream connection of breathing gas between said first point and said second point;

said anesthetic gasifier unit is connected in a sidestream configuration to said inspiratory patient gas delivery path, between said first point and said second point, for adding said gasified anesthetic agent in a desired concentration to said inspiratory patient gas delivery path at said second point, said sidestream connection between said first point and said second point insuring that the added gasified anesthetic agent does not increase said amount;

a flow generator that provides a flow of breathing gas from said first point to said breathing gas input port of said anesthetic gasifier unit; and said aggregate comprises a control unit configured to regulate said desired concentration of said gasified anesthetic agent in said inspiratory patient gas delivery path, said control unit being configured to detect a connection of said anesthetic gasifier unit to said inspiratory patient gas delivery path and a patient connected thereto, by an input of at least one of
   a) a pressure data provided by a pressure sensor that measures a pressure in said breathing gas input line,
   b) a flow data of a flow in said inspiratory patient gas delivery path, and
   c) a capnogram data related to $CO_2$ fluctuations in said inspiratory patient gas delivery path, and said control unit being configured to allow delivery of said anesthetic agent from said anesthetic gasifier unit only when said connection is detected.

23. The aggregate according to claim 22, comprising an anesthetic gas monitor for providing feedback input data for said regulation of said desired concentration of said gasified anesthetic agent in said inspiratory patient gas delivery path.

24. The aggregate according to claim 22, wherein said control unit is configured to regulate said desired concentration of said gasified anesthetic agent in said inspiratory patient gas delivery path based on a proportional ratio of a flow provided by said flow generator and a flow in said mainstream connection.

* * * * *